United States Patent [19]
Knuth

[11] Patent Number: 5,242,279
[45] Date of Patent: Sep. 7, 1993

[54] PUMP HOSE FOR A PERISTALTIC PUMP

[75] Inventor: Reinhard Knuth, Melsungen, Fed. Rep. of Germany

[73] Assignee: B. Braun Melsungen AG, Melsungen, Fed. Rep. of Germany

[21] Appl. No.: 913,840

[22] Filed: Jul. 15, 1992

[30] Foreign Application Priority Data

Aug. 7, 1991 [DE] Fed. Rep. of Germany ....... 4126087

[51] Int. Cl.⁵ .......................................... F04B 43/08
[52] U.S. Cl. ................................................ 417/474
[58] Field of Search ............... 417/474, 475, 476, 477, 417/478

[56] References Cited

U.S. PATENT DOCUMENTS

| 2,244,418 | 6/1941 | Bennet | 417/474 |
| 3,122,103 | 2/1964 | Ormsby | 417/477 |
| 3,403,631 | 10/1968 | Tangeman | 417/475 |
| 4,236,880 | 12/1980 | Archibald | 417/478 |
| 4,391,600 | 7/1983 | Archibald | 417/478 |
| 4,410,322 | 10/1983 | Archibald | 417/478 |
| 4,515,589 | 5/1985 | Austin | 417/477 |
| 4,540,350 | 9/1985 | Streicher | 417/475 |
| 4,585,399 | 4/1986 | Baier | 417/477 |
| 4,650,471 | 3/1987 | Tamari | 417/474 |
| 4,798,590 | 1/1989 | O'Leary et al. | 604/153 |
| 5,088,522 | 2/1992 | Rath et al. | 138/119 |

FOREIGN PATENT DOCUMENTS 0024431 3/1980 European Pat. Off. .
84062037 4/1984 Fed. Rep. of Germany .
3909657 8/1990 Fed. Rep. of Germany .

Primary Examiner—Richard A. Bertsch
Assistant Examiner—Peter Korytnyk
Attorney, Agent, or Firm—Spensley Horn Jubas Lubitz

[57] ABSTRACT

A pump hose for a peristaltic pump has a suction-side end and a pressure-side end. Each end is provided with a bushing integrally connected thereto and adapted for suspending attachment to the peristaltic pump by holding members. Each bushing holds a suspension device having two side plates directed to opposite sides in symmetry with the longitudinal axis of the hose and each side plate is formed with an eyelet therein. The eyelets in the side plates on the suction-side end of the hose have a different form and/or size than the eyelets in the side plates on the pressure-side end of the hose. The eyelets are adapted for mounting on fitted holding pins of the pump. The hose can be easily mounted in the pump while conforming to the correct flow direction with respect to the suction side and the pressure side of the pump, and the pump hose offers uniform conveying characteristics.

7 Claims, 3 Drawing Sheets

PUMP HOSE FOR A PERISTALTIC PUMP

BACKGROUND OF THE INVENTION

1. Field of the Invention

The invention is directed to a pump hose for a peristaltic pump, having its suction-side end and its pressure-side end provided with a bushing integrally connected thereto and being adapted for suspending attachment to the pump by use of holding members.

2. Description of Related Art

In medical applications, peristaltic pumps or hose pumps are used as infusion pumps. Such pumps are used for sterile conveyance of larger quantities of infusion liquid. The exchangeable pump hose is a low-cost disposable product distributed in sterile form with the infeed and discharge hoses of an infusion conduit mounted thereon, and is to be inserted into the pump by the user and then be disposed after use. However, for obtaining continuous conveying accuracy, the pump hose has to fulfill high demands regarding squeezability, elasticity, wear resistance and accuracy to size in longitudinal and transverse directions. The conveying volume depends on the dimensions of the cross section of the pump hose and the restoring ability of the hose. The used material must be physiologically unobjectionable, i.e. inert. It must be precluded that the material is affected by environmental influences such as temperature, atmospheric moisture, light and desinfectants.

Normally, pump hoses for peristaltic pumps are produced from highly elastic materials, e.g. silicone, with high accuracy to size. By use of separate special intermediate pieces, e.g. according to DE-GM 84 06 203, the ends of the infeed and discharge hoses of the infusion conduits have been connected to the pump hose ex factory, and the user inserts the pump hose into a channel of the peristaltic pump and fastens the intermediate pieces to holding devices of the pump housing for fixing the pump hose in its correct position. The pump hose extends between an abutment and pump sliders performing strokes against the hose and compressing it peristaltically. Since one end of the infusion conduit is connected to an infusion liquid container or the like and the other end of the infusion conduit leads to the patient, it is essential upon insertion of the pump hose into the peristaltic pump that the flow direction is correct, i.e. that the infusion container side is located on the suction side of the pump and the patient side is located on the pressure side. Up to now, the correctness of this allocation cannot be easily checked because the bushings mounted to the intermediate pieces look substantially the same and also the intermediate pieces do not allow quick conclusions regarding their respective association to the upper or lower holding devices on the channel of the pump housing.

The continued development in medical science leads to ever increasing demands to the maintenance of certain limit values in infusion technology. At the same time, the large variety of apparatuses and the high working stress of the operating staff have made it still more urgent to provide for simple identification and easy handling. Since maloperation can ultimately put the patient at risk, well-defined fixation of the pump hose has become a matter of safety in medical technology. Using the above intermediate pieces by which the bushings of the pump hose are mounted to the infeed and discharge hoses and which have to be fastened to the pump housing themselves, suffers from the disadvantage that the hose diameter and the hose length—due to tension or upsetting—and the position of the pump hose in the pump are dependent on the respective mounting process so that the conveying or infusion rate cannot be maintained at the required position but varies from one pump hose to another with a relatively large range of tolerances.

A pump hose with integrally formed bushings is disclosed in U.S. Pat. No. 5,088,522. In its undeformed state, this pump hose consists of two arcuate portions so that the hose volume has the cross sectional shape of a biconvex lens. The bushings themselves are formed as circular cylinders. By this cross-sectional shape of the pump hose, the force needed for occlusive closure of the hose by the pump sliders of the peristaltic pump is reduced. The connecting regions of the two arcuate hose wall portions have webs outwardly projecting therefrom, the thickness of said webs substantially corresponding to the sum of the thickness dimensions of the two arcuate portions. These webs serve for decreasing wear and tear of the material by taking up part of the occlusion force acting on the hose from the outside. When setting the force to be exerted on the hose, tolerances of the infusion pump are eliminated.

In a peristaltic pump disclosed in EP 0 024 431, the pump element is formed of two sheets being in face-to-face welding abutment with each other except for a central longitudinal portion. Said longitudinal portion forms a pump chamber having its underside provided with a plurality of cup-shaped flexible structures whose volume is changed by pistons for obtaining the pumping effect. The two axial ends of the longitudinal portion have an inlet hose and an outlet hose connected thereto. On a longitudinal edge of the sheet-shaped pump element, notably in the region of the ends of the pump element, there are formed a longitudinal hole and a circular hole which, when the pump element is laid onto an abutment face on the pump housing, allow passage of circular cylindrical pins projecting from the abutment face. Cooperation of the circular hole with one of the pins is intended to define the correct orientation of the pump element. Such a "push button" is of no use in a pump hose having bushings arranged at its end sides because in such a pump hose it is imperative that the hose be fixed in suspended manner without its conveying volume being affected by changes of size.

SUMMARY OF THE INVENTION

It is an object of the invention to provide a pump hose which can be easily mounted in the pump while conforming to the correct flow direction with respect to the suction side and the pressure side of the pump and which is distinguished by uniform conveying characteristics.

According to the invention, the above object is solved in that each bushing has arranged thereon a suspension device comprising two side plates directed to opposite sides in symmetry with the longitudinal axis of the hose and being each formed with an eyelet therein, that the eyelets in the side plates on the suction-side end of the hose have a different form and/or size than the eyelets in the side plates on the pressure-side end of the hose, and that the eyelets are adapted for mounting on fitted holding pins of the pump.

The suspension device and the holding pins arranged in flow direction before the pump (on the suction side), are unmistakably different from those arranged in flow direction behind the pump (on the pressure side) so that the user is not only able to unambiguously recognize the flow direction to which the hose is to be oriented but, because of the different fitting contours of the parts, is also forced to handle them in the correct manner. A simple geometry of the eyelets and the fitted holding pins facilitates the recognition of the mutual association of the apparatus-side and the hose-side fixing elements as well as the placing of the pump hose in the pump. By mounting the eyelets onto the fitted holding pins of the pump, fixing of the pump hose can be effected in a simple and correct manner. By simple suspension of the eyelets onto the fitted holding pins of the pump, the pump hose is inserted into the pump with a defined distance of the suction-side bushing from the pressure-side bushing. Thus, the longitudinal dimension depends on the tool and not on the mounting. Since the distance of the suction-side and the pressure-side fixing elements is largely free of manufacturing and mounting tolerances, undefined stretching of the hose of the pump segment is avoided and thus a high conveying accuracy is obtained. The pump operates within a narrow range of tolerances practically without variations and at the preset conveying capacity because the pump hose is neither stretched nor upset. Further advantages of the stretch-free condition of the hose reside in the avoidance of damages to the material and in improved restoring characteristics. The service life of the pump hose is extended and the constancy of the conveying volume over the infusion time is increased.

In an advantageous embodiment of the invention, it is provided that the side plates of the suction-side end together form the tip of an arrow pointing to the pressure-side end and that the side plates of the pressure-side end have rectangular shape. The pairs of side plates facilitate handling of the pump hose during insertion thereof into the pump and provide for safe hold. By the arrow-tip shape of the side plates on the suction side and the different form of the side plates on the pressure side, the flow direction is marked clearly and unmistakably.

For further assistance in precluding wrong orientation of the pump hose, it is provided that the centers of the eyelets arranged symmetrically to the longitudinal axis of the hose on the suction-side end are not in flush alignment with the centers of the eyelets arranged symmetrically to the longitudinal axis of the hose on the pressure-side end.

The eyelets in the side plates on the suction-side end can be of circular shape while the eyelets in the side plates on the pressure-side end are rectangular and have their longitudinal axes extending in parallel to the longitudinal axis of the hose. Accordingly, the fitted holding pins have a suitably adapted circular cross section on the suction-side end of the pump channel and a suitably adapted rectangular cross section on the pressure-side end of the pump channel. For preventing undesired forceful shift-on of the circular holes onto the rectangular holding pins, the width of the rectangular holding pins is considerably larger than the diameter of the circular eyelets. Preferably, the holding pins with the circular cross section are inclined upwardly so that the side plates cannot slip from the holding pins toward the front. Orientation of the lower rectangular holding pins can be substantially horizontal, with the safe hold of the hose being obtained by frictional engagement. The mutual distance of the pairs of holding pins substantially corresponds to the distance of the pairs of eyelets.

Preferably, the side plates are integrally formed to the bushings. The side plates lie in a common plane and do not project beyond the axial ends of the bushings.

Each bushing has a tubular fixing member lockingly fitted therein, the end of an infeed hose or the end of a discharge hose of the infusion conduit being fixedly inserted in said fixing member. The tubular fixing members are rigid plastic pieces stiffening the bushings made from the flexible hose material, and thus improving the correct seat of the side plates, also being flexible per se, on the holding pins.

An embodiment of the invention is schematically illustrated in the Figures.

DESCRIPTION OF THE PREFERRED EMBODIMENT

Figure 1:
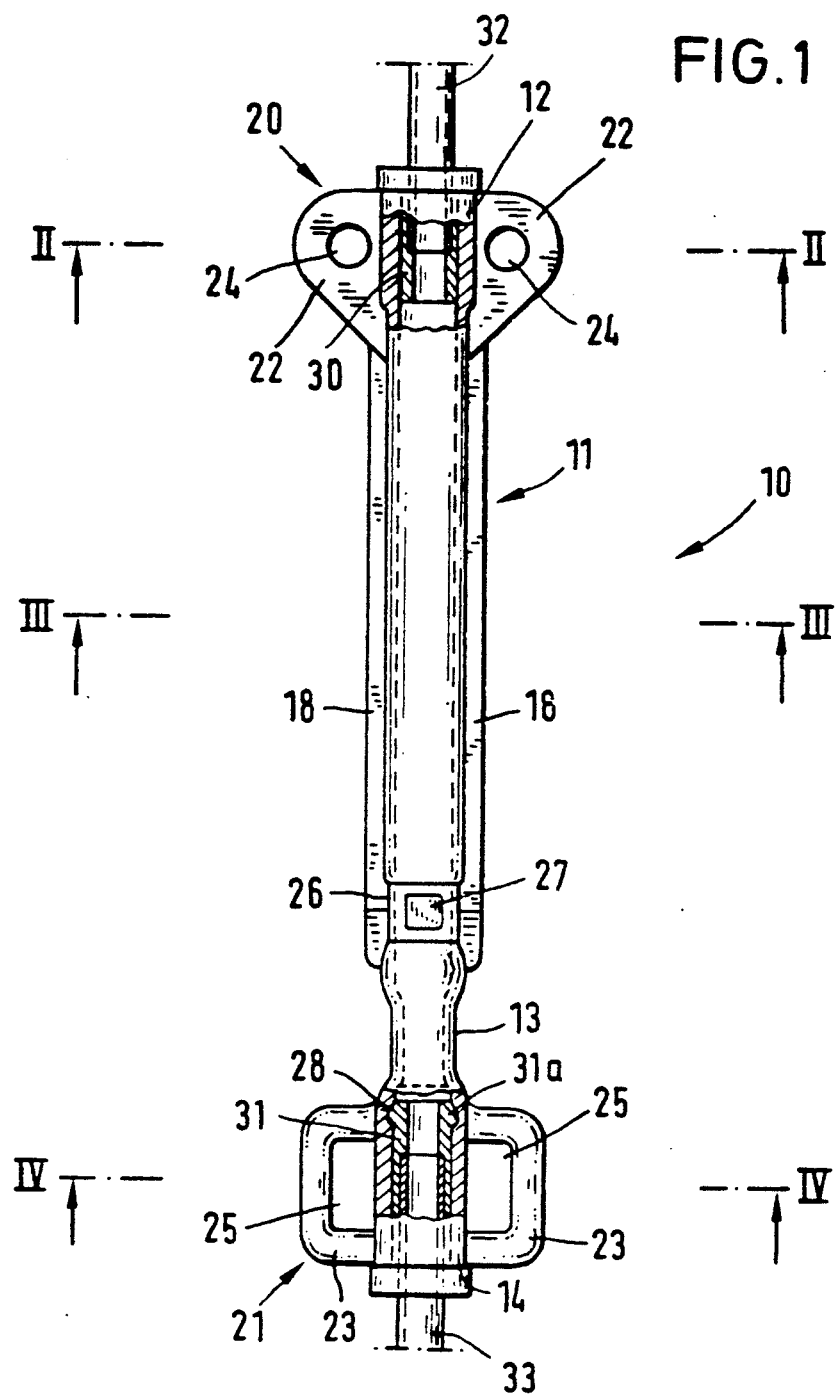
FIG. 1 shows a plan view onto a pump hose for a peristaltic pump.
Figure 2:
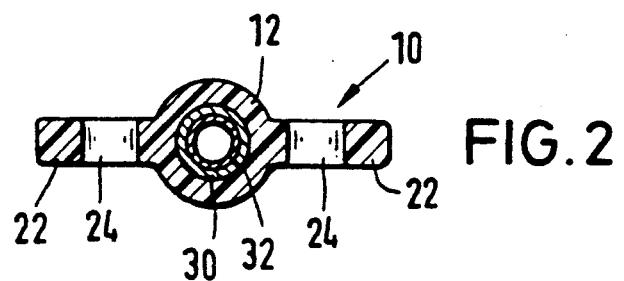
FIG. 2 shows a sectional view along the line II—II in FIG. 1.

The pump hose 10 according to FIG. 1 consists of a highly elastic material, e.g. silicone. Pump hose 10 comprises an elongated central portion 11 having its upper end provided with an integrally attached circular cylindrical bushing 12 and having its lower end provided with a cylindrical bushing 14 fastened thereto through a intermediate portion 13. When viewed in cross section, the central portion 11 of hose 10 comprises two arcuate portions 15,16 surrounding a hose lumen 17 in such a manner that said hose lumen 17 has the cross-sectional shape of a biconvex lens. The two longitudinal edges of hose 10 are joined, in the plane of the longer axis of the cross section of hose 10, by outwardly directed webs 18. The thickness of each of said webs 18 substantially corresponds to the sum of the wall thicknesses of the two arcuate portions 15,16.

Figure 3:
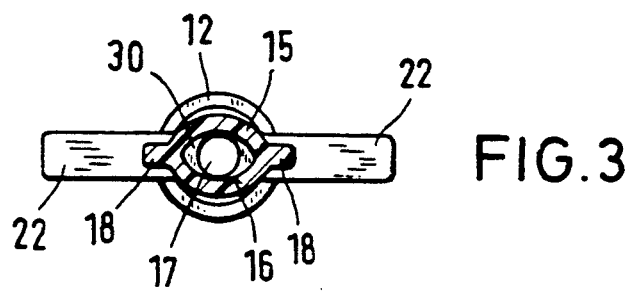
FIG. 3 shows a sectional view along the line III—III in FIG. 1.
Figure 4:
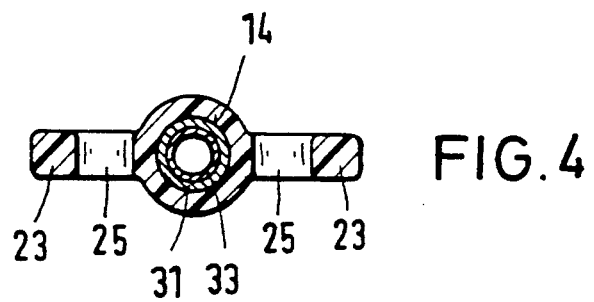
FIG. 4 shows a sectional view along the line IV—IV in FIG. 1.

Each of the bushings 12,14 is provided with a suspension means 20,21, one of said suspension means being provided for arrangement on the suction side and the other one being provided for arrangement on the pressure side in the mounted condition. One suspension means 20 comprises two identical side plates or flaps 22 which in a common plane are directed to opposite sides in symmetry with the longitudinal axis of hose 10 and which are integrally formed to the body of hose 10. Each of side plates 22 is shaped as a triangle with rounded edges, and orientation of the two side plates 22 is such that there is formed the tip of an arrow pointing to the other end of hose 10. The two side plates 22 end flush with the opening edge of bushing 12. The arrow-tip end of the two side plates 22 merges into the two webs 18 of the central portion 11 of hose 10. The respective thickness of side plates 22 is larger than that of webs 18 (FIG. 3). Each side plate 22 has formed therein an eyelet 24 shaped as a circular passage. The two eyelets 24 are arranged in symmetry to the longitudinal axis of hose 10 and their centers are located on a common line extending at a right angle to the longitudinal axis of hose 10.

The suspension device 21 at the other end of hose 10 consists of two identical side plates 23 integrally formed to bushing 14 and directed to opposite sides in symmetry with the longitudinal axis of hose 10 while being arranged in a common plane and in the plane of side plates 22. The two side plates 23 have rectangular shape with rounded outer edges. Each of side plates 23 has a rectangular eyelet 25 passing therethrough. The longitudinal axes of side plates 23 and of eyelets 25 extend parallel to the longitudinal axis of hose 10. The centers of eyelets 25 are arranged symmetrically to the longitudinal axis of hose 10 and are located on a common line extending at a right angle to the longitudinal axis of the hose. With respect to the centers of eyelets 24, the centers of eyelets 25 are not located in straight alignment below these but at a slight symmetrical displacement towards the inside. The rectangular eyelets 25 directly join the outer face of bushing 14.

Near the lower end of central portion 11 of lens-shaped cross section, the wall thickness of hose 10 is reduced, thus forming a lengthwise portion adapted for use as a pressure-measuring zone 26. A pressure sensor for detecting the internal pressure can be applied from the outside to this pressure-measuring zone 26. An outwardly projecting boss 27 on pressure-measuring zone 26 prevents damage of the hose wall under the influence of the pressure sensor.

Figure 5:
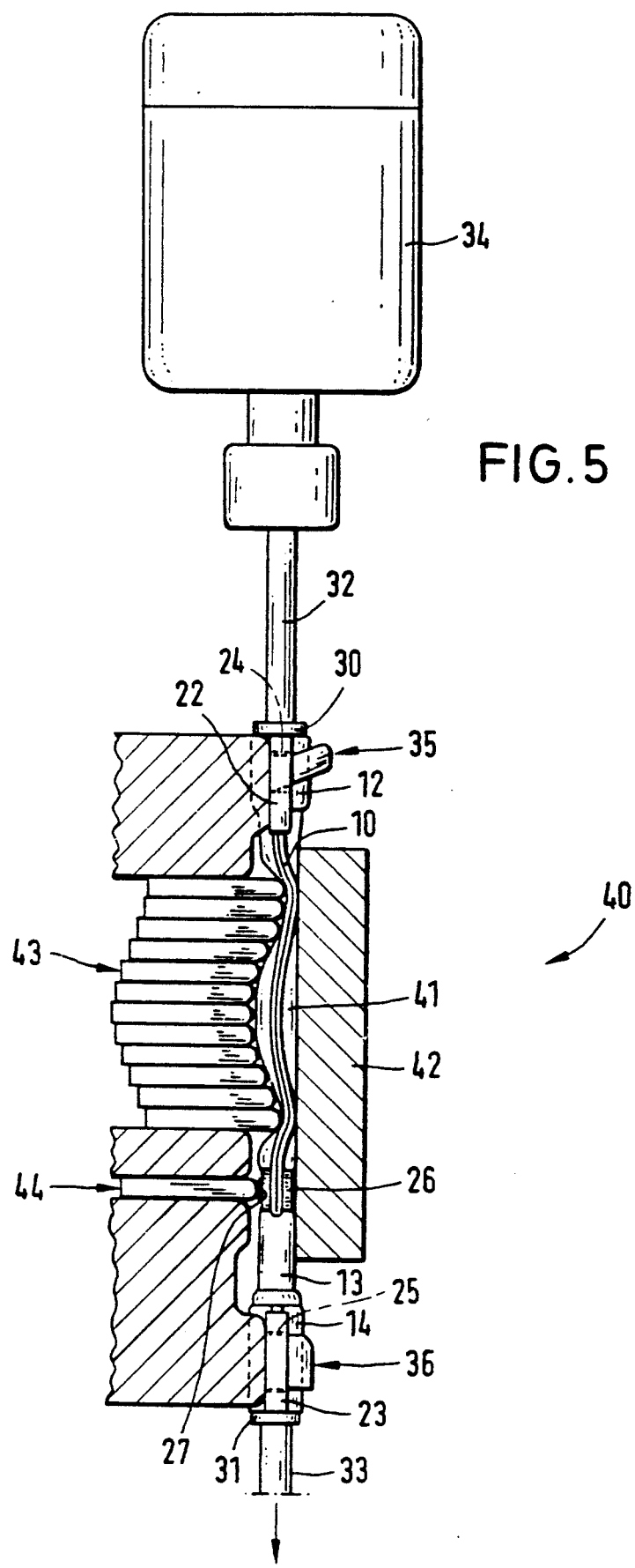
FIG. 5 shows a longitudinal sectional view through a portion of the peristaltic pump with the pump hose mounted therein.

Each of bushings 12,14 has fitted therein a tubular fixing piece 30,31 whose circular cylindrical channel serves for attachment of an inserted infeed hose 32 and a discharge hose 33; both of said hoses 32,33 form part of an infusion conduit for connecting a container 34 with infusion liquid to a patient (FIG. 5). The lower fixing piece 31 by an outer annular shoulder 31 thereof lockingly engages an annular groove 28 at the transition of the hose lumen between bushing 14 and central portion 11. Infeed hose 32 and discharge hose 33 are preferably bonded or welded into fixing pieces 30,31.

Pump hose 10 is ex factory provided with infeed hose 32 and discharge hose 33, and the user will mount the infusion conduit, having a length of up to 2 m, into a peristaltic pump 40. In doing so, it is important that the infeed hose 32 is located on the suction-side end of pump 40 and that discharge hose 33 is located on the pressure-side end of pump 40 so as to provide for the correct flow direction from said infusion liquid container 34 to the patient. When mounting the pump hose 10 into the peristaltic pump 40, the user will recognize the flow direction first by the pointing direction of the arrow tip formed by the two side plates 22. Further, the user is forced to perform the mounting procedure in the correct manner because the eyelets 24 and 25 can be plugged exclusively onto the appropriately fitted holding pins of pump 40, i.e. in case of wrong orientation of pump hose 10 and confusion of eyelets 24 and 25, the latter cannot be easily shifted onto the holding pins. The circular eyelets 24 being provided for the suction-side end of hose 10 and being arranged on top in the mounted state, have assigned thereto two holding pins 35 of circular cross section pointing obliquely upwards and being adapted in diameter to the diameter of eyelets 24 so that the latter can be shifted onto holding pins 35 practically without slack.

The pressure-side end of pump hose 10, arranged at the bottom, is fixed by means of two holding pins 36 of rectangular cross section provided on pump 40; the vertical distances of eyelets 24,25 and holding pins 35,36 being selected in a manner providing for defined stretching of hose 10, i.e. the longitudinal dimension depends on the tool and not on the mounting, and the conveying rate is constant within a narrow range of tolerances. The holding pins 36 form webs projecting at right angles to the outside from a vertical face of pump 40. The cross section of holding pins 36 is adapted for fitting into the rectangular eyelets 25. The vertical width of the holding pins 36 is considerably larger than the diameter of the circular holes 24 so that the round holes cannot be shifted onto the rectangular holding pins 36 by force. As has been the case for eyelets 24 and 25, also the mutual distances of holding pins 35 are different from those between holding pins 36, thus providing an additional safety feature for precluding misoriented mounting of pump hose 10 into pump 40.

Pump hose 10, hanging between holding pins 35 and 36, extends linearly in a straight channel 41 of pump 40. One side of pump hose 10 is supported on an abutment 42 adapted to be taken out of channel 41 for mounting and removing the pump hose 10. On the opposite side, a plurality of pump sliders 43 act on the central portion 11 of hose 10. Pump sliders 43 carry out lifting movements against central portion 11 and squeeze it tight in peristaltic manner, thereby effecting conveyance of infusion liquid from infusion liquid container 34 to the patient via pump hose 10. Drive of the pump sliders 43 can be performed by a cam shaft. A pressure sensor 44 is located in abutment against pressure-measuring zone 26 of pump hose 10.

I claim:

1. A device for a peristaltic pump, comprising:
    a first holding pin associated with the peristaltic pump, the first holding pin having a first size and a first shape,
    a second holding pin associated with the peristaltic pump, the second holding pin having a second size and a second shape, at least one of the first size and shape of the first holding pin being different than at least one of the second size and shape of the second holding pin,
    a pump hose defining a substantially longitudinal axis, a first end, and a second end,
    a first bushing associated with the second end of the pump hose,
    a second bushing associated with the second end of the pump hose,
    a first pair of opposed side plates associated with the first bushing and symmetrically disposed relative to the longitudinal axis of the pump hose, the first pair of side plates defining at least a first eyelet therein adapted for mounting on at least one of the plurality of holding pins associated with the peristaltic pump,
    a second pair of opposed side plates associated with the second bushing and symmetrically disposed relative to the longitudinal axis of the pump hose, the second pair of side plates defining at least a second eyelet therein adapted for mounting on at least one of the plurality of holding pins associated with the peristaltic pump,
    the first eyelet defining a first size and a first shape,
    the second eyelet defining a second size and a second shape,
    at least one of the first size and shape of the first eyelet being different than at least one of the second size and shape of the second eyelet,
    the first size and shape of the first eyelet and the first size and shape of the first holding pin being mutually configured so that the first eyelet is substantially securely mountable on the first holding pin, the second size and shape of the second eyelet and the second size and shape of the second holding pin being mutually configured so that the second eyelet is substantially securely mountable on the second holding pin, whereby the pump hose is substantially vertically suspendable from the holding pins in an orientation that is defined by the eyelets and the holding pins.

2. The device according to claim 1, wherein the first pair of side plates define a substantially triangular shape having an apex oriented toward the second end of the pump hose, and wherein at least one of the second pair of side plates has a substantially rectangular shape.

3. The device according to claim 1, wherein the first eyelet defines a center in spaced relationship with the longitudinal axis of the pump hose, the second eyelet defines a center in spaced relationship with the longitudinal axis of the pump hose, and wherein the distance between the center of the first eyelet and the longitudinal axis of the pump hose is unequal to the distance between the center of the second eyelet and the longitudinal axis of the pump hose.

4. The device according to claim 1, wherein the first eyelet defines a substantially circular shape and wherein the second eyelet defines a substantially rectangular shape and has a longitudinal axis extending substantially parallel to the longitudinal axis of the pump hose.

5. The device according to claim 1, wherein at least one of the first and second bushings and at least one of the first and second side plates are integrally formed.

6. The device according to claim 1, further comprising a first tubular fixing member associated with the first bushing and configured to receive an end of an infeed hose, a second tubular fixing member associated with the second bushing and configured to receive an end of a discharge hose.

7. The device according to claim 1, wherein the pump hose defines a cross section having a substantially biconvex shaped interior and a substantially biconvex shaped exterior, and at least one of the bushings defines an interior having a substantially circular cylindrical shape and an exterior having a substantially circular cylindrical shape.

* * * * *